USOO5631298A

United States Patent [19]
Anderson et al.

[11] Patent Number: 5,631,298
[45] Date of Patent: May 20, 1997

[54] GROWTH PROMOTION

[75] Inventors: David B. Anderson; Edward L. Veenhuizen, both of Greenfield, Ind.

[73] Assignee: Eli Lilly and Company, Indianapolis, Ind.

[21] Appl. No.: 449,874

[22] Filed: May 25, 1995

Related U.S. Application Data

[62] Division of Ser. No. 37,789, Mar. 18, 1993, which is a continuation of Ser. No. 606,670, Oct. 31, 1990, abandoned, which is a division of Ser. No. 328,996, Mar. 27, 1989, Pat. No. 4,992,473, and Ser. No. 153,640, Feb. 8, 1988, Pat. No. 4,849,453, which is a division of Ser. No. 860,719, May 7, 1986, Pat. No. 4,734,437, which is a continuation of Ser. No. 628,002, Jul. 5, 1984, abandoned, which is a continuation of Ser. No. 462,587, Jan. 31, 1983, abandoned.

[51] Int. Cl.$^6$ .................. A61K 31/135; A61K 31/70; A61K 31/65; A61K 31/43

[52] U.S. Cl. .................. 514/653; 514/8; 514/30; 514/152; 514/199; 514/200

[58] Field of Search .................. 514/653, 199, 514/200, 30, 8, 152

[56] References Cited

U.S. PATENT DOCUMENTS

| 3,818,101 | 6/1974 | Baile et al. ...................... 514/653 |
| 4,391,826 | 7/1983 | Mills et al. ...................... 514/653 |

FOREIGN PATENT DOCUMENTS

| 0007205 | 2/1979 | European Pat. Off. . |
| 0049728 | 1/1981 | European Pat. Off. . |
| 0026298 | 4/1981 | European Pat. Off. . |
| 67/3994 | 7/1967 | South Africa . |
| 79/3296 | 2/1981 | South Africa . |
| 2028801 | 3/1980 | United Kingdom . |

OTHER PUBLICATIONS

Dijk, et al., *Recueil* 92, pp. 1281–1297 (1973).
*Fed. Proc.* 42 #3 (1983).
*Fed. Proc.* 42 #4 (1983).

*Primary Examiner*—Kevin E. Weddington
*Attorney, Agent, or Firm*—Paul R. Cantrell; Kathleen R. S. Page; David E. Boone

[57] ABSTRACT

β-Phenethanolamines are effective in promoting growth and improving feed efficiency and leanness in animals.

8 Claims, No Drawings

GROWTH PROMOTION

This application is a divisional of Ser. No. 08/037,789 filed Mar. 18, 1993 which is a continuation of application Ser. No. 07/606,670 filed Oct. 31, 1990, which is now abandoned; which is a divisional of application Ser. No. 07/328,996 filed Mar. 27, 1989, now U.S. Pat. No. 4,992,473, and issued application Ser. No. 07/153,640 filed Feb. 8, 1988 and issued Jul. 18, 1989, as U.S. Pat. No. 4,849,453; this is a divisional of application Ser. No. 06/860,719 filed May 7, 1986 and issued Mar. 29, 1988 as U.S. Pat. No. 4,734,437; this is a continuation of application Ser. No. 06/628,002 filed Jul. 5, 1984 which is now abandoned; which is a continuation of application Ser. No. 06/462,587 filed Jan. 31, 1983 which is now abandoned.

BACKGROUND OF THE INVENTION

The chemistry and use of β-phenethanolamines has been extensively investigated. A number of these compounds have been reported to have beneficial cardiac activities; see U.S. Pat. No. 3,987,200. Such compounds also are known to have sympathomimetic activity, and have found utility as utero-relaxing agents; Van Dijk et al., *Recueil*, 92, 1281 (1973). More recently, a group of β-phenethanolamines have been reported as possessing anti-hyperglycemic activity, and have been found effective in promoting the loss of weight in animals, EPO 6735 published Jan. 9, 1980.

An object of this invention is to provide a new use for certain β-phenethanolamines. This invention provides a method for promoting the growth of domesticated animals employing β-phenethanolamines.

SUMMARY OF THE INVENTION

This invention provides a method for increasing weight gain in animals and improving the efficiency of feed utilization and the quality of the carcass. The invention is more particularly directed to a method for promoting growth and improving feed efficiency and leanness comprising administering an effective amount of a compound having the formula

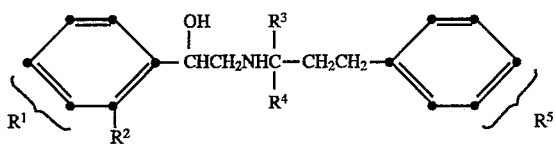

wherein:
$R^1$ is hydrogen, hydroxy, or methoxy;
$R^2$ is hydrogen or fluoro,
$R^3$ is hydrogen or $C_1$–$C_2$ alkyl;
$R_4$ is hydrogen or methyl;
$R^5$ is hydrogen, fluoro, nitro, hydroxy, $SO_2CH_3$ or $CONH_2$; provided that $R^1$ is hydrogen only when $R^5$ is nitro or $SO_2CH_3$; and the acid addition salts thereof.

A preferred method for promoting growth and improving feed efficiency and leanness according to this invention employs a compound of the above formula wherein $R^1$ is hydroxy, $R^2$ is hydrogen, $R^3$ is hydrogen or methyl and $R^4$ is methyl. The method is most preferably practiced employing a compound wherein $R^1$ and $R^5$ both are hydroxy and $R^2$ and $R^3$ both are hydrogen and $R^4$ is methyl. When $R^1$ is hydroxy or methoxy, it preferably is in the para position. When $R^5$ is other than hydrogen, it also is preferably in the para position.

This invention also provides an animal feed-stuff comprising a β-phenethanolamine of the above formula together with a suitable carrier therefor.

DETAILED DESCRIPTION OF THE INVENTION

The compounds employed in the method provided by this invention are either known in the art or are readily prepared by well known synthetic procedures. A particularly preferred method employs 1-(3-hydroxy-phenyl)-2-[1-methyl-3-(4-hydroxyphenyl)propylamino]-ethanol. This β-phenethanolamine is disclosed in South African Patent No. 673,994 published in May, 1967. The most preferred embodiment of this invention employs 1-(4-hydroxyphenyl)-2-[1-methyl-3-(4-hydroxyphenyl)-propylamino]ethanol, a compound disclosed as having utero-relaxing activity by Van Dijk et al. in *Recueil*, 92 1281 (1973).

The compounds to be employed in the method of this invention are readily prepared by reaction of a styrene oxide with a 3-phenylpropylamine derivative. For example, a styrene oxide such as 2-fluorostyrene oxide can be reacted with about an equimolar quantity of an amine such as 1-methyl-3-(4-nitrophenyl)propyl-amine in an unreactive organic solvent such as ethanol, methanol, 5-propanol, dioxane, or the like. The reaction generally is carried out at a temperature of about 50° to about 120° C., and at such temperature the reaction routinely is substantially complete within about 6 to about 10 hours. The product, a β-phenethanolamine, is readily isolated by simply removing the reaction solvent, for instance by evaporation under reduced pressure, and further purification can be accomplished if desired by standard techniques, including crystallization, chromatography, acid-base extraction, and the like.

An alternative method for preparing the β-phenethanolamines to be employed in the present method comprises reacting a mandelic acid derivative with a 3-phenylpropylamine derivative to provide an amide, which upon subsequent reduction provides a compound of the above formula. For example, a phenylpropylamine derivative such as 1-methyl-3-(3-fluorophenyl)propylamine can be reacted with an acylating agent such as a hydroxy protected mandelic acid halide, or preferably simply reacted with a mandelic acid in the presence of a common peptide coupling reagent such as N,N'-di-cyclohexylcarbodiimide, carbonyldiimidazole, N-ethoxy-carbonyl-2-ethoxy-1,2-dihydroquinoline, commonly referred to as EEDQ. The direct coupling reaction generally is conducted in an organic solvent such as benzene or N,N-dimethylformamide, and normally is complete after about 2 to 48 hours when carried out at about –30° to about 100° C. The product is an amide that is readily isolated by simply filtering the reaction mixture and then removing the reaction solvent. The amide thus formed is next reduced by reaction with a common reducing agent such as diborane or the like to provide a β-phenethanolamine defined by the above formula.

A similar, yet alternative method of synthesis comprises reacting a phenethanolamine with a phenylethyl ketone to provide a Schiff base, which upon reduction gives a compound to be employed in the present method. For example, a phenethanolamine such as 2-hydroxy-2-(4-hydroxyphenyl)ethylamine can be reacted with a ketone such as methyl 2-(4-hydroxyphenyl)ethyl ketone to provide the corresponding imine, which upon reduction, for instance with 5% palladium on carbon, provides 1-(4-hydroxyphenyl)-2-[1-methyl-3-(4-hydroxyphenyl)propylamino]ethanol.

It should be noted that the compounds to be employed in the method of this invention possess at least one asymmetric center (i.e. the carbinol center), and when $R^3$ and $R^4$ differ, the compounds possess two asymmetric centers. Since employment of individual optical isomers necessitates preparing the β-phenethanolamines from optically active starting materials, or using costly separation procedures, a preferred embodiment of this invention employs a mixture of optical isomers. For example, 1-(4-hydroxyphenyl)-2-[1-methyl-3-(4-hydroxyphenyl)propytamino]ethanol is preferably prepared from racemic mixtures of starting materials, e.g. dl-1-methyl-3-(4-hydroxyphenyl)propyl-amine and dl-4-hydroxystyrene oxide, to provide a mixture of all four possible optical isomers of the product. The mixture of optical isomers is employed in the method without subsequent separation of isomers.

Since the β-phenethanolamines to be employed in the present method are inherently basic, they readily form acid addition salts with any number of inorganic and organic acids. These salts can be employed in the method of the invention, and often are preferred to the free base since they generally are more soluble in solvents such as water and are more conveniently formulated as an animal feedstuff. Acids commonly employed to form acid addition salts include mineral acids such as hydrochloric acid, sulfuric acid, phosphoric acid, perchloric acid and the like; and organic acids such as acetic acid, citric acid, succinic acid, para-toluene sulfonic acid, methanesulfonic acid, lactic acid and the like. Preferred salts to be employed in the present method include the hydrochlorides and hydrobromides.

Typical β-phenethanolamines to be employed in the method of this invention include the following:

1-(3-hydroxyphenyl)-2-[1-methyl-1-ethyl-3-(4-aminocarbonylphenyl) propylamino]ethanol;

1-(2-fluoro-4-hydroxyphenyl)-2-[1-methyl -3-(4-fluorophenyl) propylamino]ethanol;

1-(4-hydroxyphenyl)-2-[3-(3-nitrophenyl) propylamino] ethanol;

1-(3-hydroxy-2-fluorophenyl) -2-[3-(4-methyl-sulfonyl) propylamino]ethanol;

1-(4-methoxyphenyl) -2-[1-methyl-3-(4-hydroxyphenyl) propylamino]ethanol;

1-phenyl-2-[1,1-dimethyl-3-(3-methylsulfonylphenyl) propyl amino]ethanol;

1-(4-hydroxyphenyl)-2-[1,1-dimethyl-3-(4-hydroxyphenyl) propylamino]ethanol hydrochloride;

1-(phenyl)-2-[1-methyl-3-(4-nitrophenyl)-propylamino] ethanol;

1-(3-hydroxyphenyl)-2-[1-methyl-3-(4-fluorophenyl) propylamino]ethanol succinate;

1-(4-hydroxyphenyl)-2-[1-methyl-1-ethyl-3-(4-aminocarbonylphenyl) propylamino]ethanol;

1-(4-hydroxyphenyl)-2-[1,1-dimethyl-3-phenyl- propylamino]ethanol hydrobromide; and d-1-(4-hydroxyphenyl) -2-[1,1-dimethyl-3-(4-hydroxyphenyl)propylamino]ethanol.

The method of promoting growth and improving leanness and feed efficiency provided by this invention is practiced by administering an effective amount of a compound defined above to a warm-blooded animal that receives a nutritionally adequate diet. The method generally will be practiced on domesticated animals raised for human meat consumption, for example grower/finisher swine, poultry, ruminants and the like. In a preferred embodiment, the growth of pigs, chickens and turkeys is promoted employing a β-phenethanolamine. Another preferred embodiment is practiced in ruminants such as cattle, sheep and goats. The method of improving leanness is not limited to meat producing animals, and can be practiced on other warm-blooded animals, including dogs and cats. This latter embodiment is particularly useful when it is desired to maintain mature animals in a relatively lean physical state.

The method of the invention is preferably practiced by orally administering an effective amount of a β-phenethanolamine to an animal. Other routes of administration can be employed, for instance intra-muscular or intravenious injection; however, such routes are less practical. The amount to be administered to an animal is an amount that is effective in causing a promotion of growth, or an improvement in the efficiency of utilization of food, or an improvement in carcass quality of the animal, for instance in the form of less fatty tissue and improved leanness. The effective amount to be administered will vary somewhat depending upon the particular animal species being treated and the particular active ingredient employed, but generally will be from about 1 to about 1000 parts per million (ppm) of total daily feed intake. Such amount will provide a dosage of about 0.05 to about 50 mg/kg. A preferred embodiment employs about 1 to about 200 ppm, and more preferably from about 5 to about 100 ppm. A typical amount of active ingredient to be administered to swine will be from about 5 to about 40 ppm. For example, when practicing the method in animals such as ruminants or swine, the compound will be added to the daily feed ration at about 5 to about 100 parts per million of the daily feed ration.

For oral administration, the active β-phenethanolamine is preferably admixed with suitable carriers or diluents commonly employed in animal husbandry. Animal feedstuffs comprising a β-phenethanolamine growth promoter as defined herein are provided as a further embodiment of this invention. Typical carriers and diluents commonly employed in such feedstuffs include corn meal, soybean meal, alfalfa meal, rice hulls, soybean mill run, cottonseed oil meal, bone meal, ground corn, corncob meal, sodium chloride, urea, cane molasses and the like. Such carriers promote a uniform distribution of the active ingredient in the finished feed ration into which such compositions are added, thereby ensuring proper distribution of the active ingredient throughout the feed. The feedstuff composition provided by the invention will contain about 5 to about 95 percent by weight of active ingredient, and more typically about 10 to about 50 percent by weight. As already noted, the acid addition salts of the active phenethanolamines are generally preferred for oral administration, and are thus the preferred form of active ingredient for the feedstuff compositions of the invention.

While the preferred method for orally administering the growth promoters is via the daily feed rations, the compounds can be incorporated into salt blocks and mineral licks, as well as being added directly to drinking water for convenient oral consumption. The compounds can additionally be formulated with polymorphous materials, waxes and the like for long-term controlled release, and administered to an animal as a bolus or tablet only as needed to maintain the desired daily payout of active ingredient.

For parenteral administration, the β-phenethanolamines can be admixed with conventional carriers such as corn oil, sesame oil, carbowax, calcium stearate and the like. Such formulations can be molded into pellets and administered as an injection or as a slow-release subcutaneous implant. Such administrations can be made as often as needed to ensure the proper dosing of active ingredient to obtain the desired rate of growth promotion and improvement in leanness and feed efficiency.

While the compounds described herein are effective in promoting average daily weight gain and improving feed efficiency in animals, they also cause observable improvement in the quality of the meat produced. For example, the compounds appear to mobilize free fatty acids from fatty tissue and depress the deposition of fat as the animals gain weight. This reduction of fat is beneficial since the animal being treated according to the invention gains weight in the form of more useable lean meat, thereby reducing waste and improving the value of the animal thus treated. Also, mature animals that are not subject to additional weight gain can be maintained in a desirably lean form by administering a compound as described herein.

The practice of the present invention is more fully illustrated by the following detailed examples.

EXAMPLE 1

Preparation of dl-4-(benzyloxy)mandelic acid

A solution of 5.0 g of dl-4-hydroxy mandelic acid, 11.0 g of benzyl chloride and 10.0 g of potassium carbonate in 50 ml of methanol was heated to reflux and stirred for seventy-two hours. The reaction mixture was cooled to room temperature and diluted with 50 ml of water. The aqueous solution was washed twice with 50 ml portions of benzene, and then was acidified with concentrated hydrochloric acid. The aqueous acid solution was extracted three times with 50 ml portions of ethyl acetate. The organic extracts were combined, washed with water and with saturated sodium chloride solution and dried. Removal of the solvent by evaporation under reduced pressure provided 5.7 g of a solid which was then recrystallized from 300 ml of toluene to afford 5.33 g of dl-4-(benzyloxy)mandelic acid. M.P. 153°–155° C.

Analysis calc. for $C_{15}H_{14}O_4$
Theory: C, 69.76; H, 5.46;
Found: C, 69.96; H, 5.33.

EXAMPLE 2

Resolution of dl-4-(benzyloxy)mandelic acid to provide R(−)-(4-benzyloxy)mandelic acid To a stirred solution of 185.6 g of dl-4-benzyloxy) mandelic acid in 2500 ml of ethyl acetate at 80° C. was added in one portion 43.6 g of R(+)-α-methyl-benzylamine. The reaction mixture was cooled to room temperature, and the precipitated solid which had formed was collected by filtration and washed with fresh ethyl acetate. The solid was recrystallized twice from a solution of ninety percent ethanol in water to provide 91.4 g of the R(+)-α-methylbenzylamine salt of R(−)-4-(benzyloxy)mandelic acid. M.P. 208.5°–209.5° C. $[\alpha]_D$–38.6°, $[\alpha]_{365}$–155.3° (MeOH)

Analysis calc. for $C_{23}H_{25}NO_4$
Theory: C, 72.80; H, 6.64; N, 3.69;
Found: C, 72.95; H, 6.83; N, 3.95.

To a stirred suspension of 91.4 g of the above-named salt in 2000 ml of ethyl acetate was added 150 ml of ten percent aqueous hydrochloric acid solution. The aqueous acid solution was separated, and the organic layer washed with water and dried. Removal of the solvent by evaporation under reduced pressure afforded 54.5 g of R(−)-4-(benzyloxy) mandelic acid, i.e. 30 R(−)-2-(4-benzyloxyphenyl)-2-hydroxyacetic acid. M.P. 155°–161° C. $[\alpha]_D$–102.2°; $[\alpha]_{365}$–410.6° (MeOH)

Analysis calc. for $C_{15}H_{14}O_4$
Theory: C, 69.76; H, 5.46;
Found: C, 69.67; H, 5.41.

EXAMPLE 3

Preparation of dl-1-methyl-3-(4-benzyloxyphenyl) propylamine

A solution of 40.0 g of methyl 2-(4-benzyloxyphenyl) ethyl ketone and 160 ml of anhydrous ammonia in 300 ml of ethanol was heated at 75° C. and stirred for two hours. After cooling the reaction mixture to room temperature, 4.0 g of Raney nickel was added in one portion, and the reaction mixture then was stirred at 25° C. for twelve hours under a hydrogen atmosphere at 300 psi. The reaction mixture next was filtered and the filtrate was concentrated by evaporation of the solvent under reduced pressure to provide an oil. The oil was dissolved in 120 ml of 3N hydrochloric acid, from which the product as a hydrochloride salt precipitated. The salt so formed was collected by filtration and recrystallized from methanol and toluene to provide 36.2 g of dl-1-methyl-3-(4-benzyloxyphenyl)propylaminium chloride. M.P. 195°–197.5° C.

EXAMPLE 4

Resolution of di-1-methyl-3-(4-benzyloxyphenyl) propylamine to provide R-(−)-1-methyl-3-(4-benzyloxyphenyl)propylamine A solution of 629.3 g of dl-1-methyl-3-(4-benzyloxyphenyl)propylaminium chloride was converted to the free amine by reaction with 95 g of sodium hydroxide in 400 ml of water. The free amine was then dissolved in 2000 ml of methylene chloride and added to a solution of 328 g of D-(−)-mandelic acid in 1000 ml of methanol. The mandelic acid salt of the free amine precipitated out of solution and was recrystallized three times from methanol to provide 322 g of the R-mandelic acid salt of R-1-methyl-3-(4-benzyloxyphenyl)propylamine. M.P. 166°167° C. $[\alpha]_D$–30°, $[\alpha]_{365}$–119° (MeOH).

The salt so formed was converted to R-1-methyl-3-(4-benzyloxyphenyl)propylamine as the free base by reaction with aqueous sodium hydroxide.

EXAMPLE 5

R,R-N-[2-(4-Benzyloxyphenyl)-2-hydroxy-1-oxoethyl]-1-methyl-3-(4-benzyloxyphenyl) propylamine A solution of 93.9 g of R-1-methyl-3-(4-benzyloxyphenyl)propylamine in 500 ml of N,N-dimethylformamide containing 63.0 g of 1-hydroxybenzotriazole and 104.6 g of R-2-(4-benzyloxyphenyl)-2-hydroxyacetic acid was cooled to 0° C. and stirred while a solution of 83.6 g of N,N'-dicyclohexylcarbodiimide in 300 ml of dimethylformamide was added dropwise over one hour. The reaction mixture was stirred for twelve hours at 3° C. and then was diluted with 10 ml of water, stirred for an additional hour, and then cooled to −30° C. in an ice-acetone bath. The reaction mixture was filtered to remove dicyclohexylurea, and then the filtrate was concentrated by evaporation of the solvent under reduced pressure. The concentrated solution was diluted with ethyl acetate and washed with saturated aqueous sodium carbonate solution, with water, with 300 ml of 1N hydrochloric acid, and again with water. The organic layer was dried and the solvent was removed by evaporation under reduced pressure to provide the product as a white solid. The solid was recrystallized once from acetonitrite and again from methanol to provide 159.7 g of R,R-N-[2-(4-benzyloxyphenyl)-2-hydroxy-1-oxoethyl]-1-methyl-3-(4-benzyloxyphenyl)-propylamine. M.P. 145°–148° C. $[\alpha]_D$–15.9°, $[\alpha]_{365}$–50.1° (MeOH).

Analysis calc for $C_{32}H_{33}NO_4$
Theory: C, 77.55; H, 6.71; N, 2.83;
Found: C, 77.04; H, 6.84; N, 2.53.

EXAMPLE 6

R,R-N-[2-(4-Benzyioxyphenyl)-2-hydroxyethyl]-1-methyl-3-(4-benzyloxyphenyl)propylamine To a stirred solution of 10.0 g of R,R-N-[2-(4-benzyloxyphenyl)-2-hydroxy-1-oxoethyl]-1-methyl-3-(4-benzyloxyphenyl)propylamine in 500 ml of freshly distilled tetrahydrofuran under a nitrogen gas atmosphere was added dropwise over thirty minutes 41 ml of 2 molar borane-dimethyl sulfide complex in tetrahydrofuran. The reaction mixture was stirred at 25° C. for twenty hours, and then was heated to reflux and stirred for an additional three hours. After cooling the reaction mixture to 25° C. and stirring for another eighteen hours, the excess borane was decomposed by the slow portion-wise addition of 400 ml of methanol. The solvent was then removed from the reaction mixture by evaporation under reduced pressure to provide the product as an oil. The oil so formed was dissolved in 250 ml of hot methanol, and after concentrating the volume to 125 ml, the product began crystallizing out of solution. The crystalline product was collected by filtration and recrystallized twice from methanol to provide 6.65 g of R,R-N-[2-(4-benzyloxyphenyl)-2-hydroxyethyl]-1-methyl-3-(4-benzyloxyphenyl)propylamine. M.P. 119°–123.5° C.

The amine so formed was dissolved in methanol and added to a solution of ethereal hydrogen chloride, thereby providing 6.49 g of R,R-N-[2-(4-benzyloxy-phenyl)-2-hydroxyethyl]-1-methyl-3-(4-benzyloxyphenyl)-propylaminium chloride. M.P.214.5°–216° C. $[\alpha]_D$–13.4°, $[\alpha]_{365}$–30.2° (MeOH).

Analysis calc. for $C_{32}H_{36}NO_3Cl$
Theory: C, 74.19; H, 7.00; N, 2.70; Cl, 6.84;
Found: C, 74.20; H, 6.98; N, 2.65; Cl, 6.63.

EXAMPLE 7

R, R-1-(4-Hydroxyphenyl) -2-[1-methyl-3-(4-hydroxyphenyl) propylamino]ethanol hydrochloride, also named as R,R-N-[2- (4-Hydroxyphenyl) -2-hydroxyethyl]-1-methyl-3- (4-hydroxyphenyl) propylaminium chloride A mixture of 51.6 g of R, R-N-[2-(4-benzyl-oxyphenyl) -2-hydroxyethyl]-1-methyl-3-(4-benzyloxy-phenyl) propylaminium chloride and 5.0 g of Raney nickel in 2 liters of ethanol and 2 liters of ethyl acetate was stirred at 25° C. for four and one-half hours under a hydrogen atmosphere of 60 psi. The reaction mixture was then filtered to remove the residual Raney nickel, and the filtrate was concentrated to an oil by evaporation of the solvent under reduced pressure, and the oil was crystallized from fresh ethanol and diethyl ether to provide 29.8 g of R,R-N-[2-(4-hydroxyphenyl)-2-hydrcxyethyl]-1-methyl-3-(4-hydroxyphenyl) propylaminium chloride. M.P. 176°–176.5° C. (dec.) $[\alpha]_D$–22.7°, $[\alpha]_{365}$–71.2° (3.7 mg/ml MeOH).

Analysis calc. for $C_{18}H_{24}NO_3Cl$
Theory: C, 63.99; H, 7.16; N, 4.15;
Found : C, 63.70; H, 7.26; N, 4.32.

EXAMPLE 8

As pointed out above, a preferred embodiment of this invention employs a mixture of all four optical isomers of the compound of Example 7. This racemic mixture can be prepared by the method described above by reaction of dl-4-(benzoyloxy)mandelic acid with dl-1-methyl-3-(4-benzyloxyphenyl)propylamine in the presence of DCC to give racemic 1-(4-benzyloxyphenyl)-2-oxo-2-[1-methyl-3-(4-benzyloxyphenyl)propylamino]ethanol. Reduction of the latter compound and subsequent removal of the benzyl groups provides racemic 1-(4-hydroxy-phenyl)-2-[1-methyl-3-(4-hydroxyphenyl)propylamino]-ethanol. This compound is more preferably prepared by the following procedure.

A solution of 32.8 g. (0.2 m) of methyl 2-(4-hydroxyphenyl)ethyl ketone and 42.6 g. (0.2 m) of 1-(4-hydroxyphenyl)-2-aminoethanol in 380 ml. of ethanol containing 3.8 g. of five percent palladium on carbon was stirred for sixteen hours at 60° C. under hydrogen at 55 psi. The reaction mixture was then filtered, and the filtrate was diluted by addition of 350 ml. of water. The aqueous mixture was concentrated to a volume of about 400 ml., and then washed with dichlorcmethane. The aqueous mixture was acidified by addition of 50 ml. of conc. hydrochloric acid. After standing at room temperature for two hours, the aqueous acid mixture was filtered and the filter cake was washed with 40 ml. of ice water and dried at 50° C. in vacuum to provide 47 g. of 1-(4-hydroxyphenyl-2-[1-methyl-3-(4-hydroxyphenyl)propylamino]ethanol hydrochloride. M.P. 124°–129° C.

Analysis calc. for $C_{18}H_{24}NO_3Cl$
Theory: C, 63.99; H, 7.16; N, 4.15; Cl, 10.49.
Found: C, 63.77; H, 6.80; N, 3.91; Cl, 10.68.

$^{13}C$ NMR studies demonstrated the product to be comprised of 51% RR,SS diastereamer and 49% RS,SR diastereomer.

EXAMPLE 9

1-Phenyl-2-[1-methyl-3-(4-nitrophenyl)propylamino]ethanol

A solution of 5.0 g. (25.9 mM) of 2-amino-1-phenyletkanol and 3.55 g. (25.9 mM) of methyl 2-(4-nitrophenyl)ethyl ketone in 60 ml. of toluene containing 10 mg. of para-toluenesulfonic acid was heated at reflux for six hours in a flask equipped with a Dean-Stark trap. The water that formed during the reaction was removed via the trap, and then the reaction mixture was cooled to room temperature and concentrated to dryness by evaporation of the solvent under reduced pressure. The solid product that remained was dissolved in 50 ml. of tetrahydrofuran and the solution was heated to reflux. A solution of 13.5 ml. of 2N borane-methyl sulfide complex in tetrahydrofuran was then added dropwise to the reaction mixture, and the mixture was refluxed for an additional ninety minutes. After cooling the reaction mixture to room temperature, it was diluted by addition of diethyl ether saturated with hydrogen chloride. The precipitate that formed was collected by filtration and crystallized from ethanol and diethyl ether to give 3.29 g. of 1-phenyl-2-[1-methyl-3-(4-nitrophenyl)-propylamino] ethanol hydrochloride. M.P. 203°–213° C.

Analysis calc. for $C_{18}H_{23}ClN_2O_3$
Theory: C, 61.62; H, 6.61; N, 7.98; Cl, 10.11.
Found: C, 61.76; H, 6.62; N, 7.76; Cl, 10.13.

EXAMPLE 10

1-(4-Hydroxyphenyl)-2-[1,1-dimethyl-3-phenyl-propylamino]ethanol

A solution of 32.6 g. (0.2 m) of 1,1-dimethyl-3-phenylpropylamine and 22.9 g. (0.1 m) of 2-(4-methoxyphenyl)-2-oxoethyl bromide in 75 ml. of tetrahydrofuran was heated at reflux for thirty-six hours. The reaction mixture was then cooled and added to 2 liters of diethyl ether. The precipitate was removed by filtration, and the filtrate was acidified with hydrobromic acid to give 18.15 g. of 1-(4-methoxyphenyl)-1-oxo-2-(1,1-dimethyl-3-phenylpropylamino)ethane hydrobromide. M.P. 174°–178° C.

The compound thus formed was dissolved in 85 ml. of glacial acetic acid containing 35 ml. of hydrobromic acid, and the solution was heated at reflux for nine hours. The solution was then cooled and the solvent was removed by evaporation to provide, following crystallization from ethanol and diethyl ether, 7.8 g. of 1-(4-hydroxyphenyl)-1-oxo-2-(1,1-dimethyl-3-phenyl-propylamino)ethane hydrobromide. M.P. 228°–230° C.

Catalytic hydrogenation of 5.0 g. of the compound from above in 44 ml. of ethanol containing 1.25 g. of five percent palladium on carbon afforded, following crystallization from acetone and diethy ether, 2.3 g. of 1-(4-hydroxyphenyl)-2-(1,1-dimethyl-3-phenylpropylamino)ethanol hydrobromide. M.P. 168°–170° C.

Analysis calc. for $C_{19}H_{26}BrNO_2$
Theory: C, 60.00; H, 6.89; N, 3.68.
Found: C, 60.28; H, 6.67; N 3.62

EXAMPLE 11

1-(3-Hydroxyphenyl)-2-[1,1-dimethyl-3-(4-fluorophenyl)propylamino]ethanol

To a stirred solution of 67.2 g. (0.22M) of 2-(3-benzyloxyphenyl)-2-oxoethyl bromide in 200 ml. of acetonitrile was added a solution of 54.3 g. (0.20M) of N-benzyl-1,1-dimethyl-3-(4-fluorophenyl)propylamine in 600 ml. of acetonitrile containing 42 ml. (0.22M) of diisopropylethylamine. The reaction mixture was stirred for about six hours at reflux, and then was cooled and stored at room temperature for forty-eight hours. The reaction mixture was next diluted by addition of aqueous sodium hydroxide, and the organic solvents were removed by evaporation under reduced pressure. The aqueous alkaline mixture was extracted with ethyl acetate, which was then washed with water, dried, and concentrated to dryness to give an oil. The oil was dissolved in ethanol and diethyl ether and converted to the hydrochloride salt by addition of excess hydrogen chloride. The precipitated solid was collected by filtration and recrystallized from ethyl acetate to give 51.3 g. of 1-(3-benzyloxyphenyl)-1-oxo-2-[(N-benzyl)-1,1-dimethyl-3-(4-fluorophenyl)-propylamino]ethane hydrochloride. M.P. 137°–145° C.

The compound thus prepared was reduced by reaction with 16 g. of sodium borohydride in ethanol. Isolation of the product, followed by conversion to the hydrochloride salt and crystallization from diethyl ether afforded 55.0 g. of 1-(3-benzyloxyphenyl)-2-[(N-benzyl)-1,1-dimethyl-3-(4-fluorophenyl)propyl-amino]ethanol hydrochloride. M.P. 186.5°–191° C.

A solution of 10.0 g. of the product thus produced in 200 ml. of ethanol containing 3.0 g. of Raney Nickel was shaken for two hours at 25° C. under hydrogen at 44 psi. The reaction mixture was then filtered, and the solvent was removed from the filtrate by evaporation under reduced pressure to give a white solid. The solid was triturated with ethyl acetate and air dried to provide 5.9 g. of 1-(3-hydroxyphenyl)-2-[1,1-dimethyl-3-(4-fluorophenyl)propylamino]ethanol hydrochloride. M.P. 196.5°–198.5° C.

Analysis calc. for $C_{19}H_{25}ClFNO_2$
Theory: C, 64.49; H, 7.12; N, 3.96; Cl, 10.02.
Found: C, 64.29; H, 6.97; N, 4.06; Cl, 9.89.

EXAMPLE 12

1-(4-Hydroxyphenyl)-2-[1,1-dimethyl-3-(4-aminocarbonylphenyl)propylamino]ethanol A suspension of 10.0 g. (50 mM) of 1,1-dimethyl-3-(4-aminocarbonylphenyl)propylamine and 15.0 g. (50 mM) of 1-(4-benzyloxyphenyl)-1-oxoethyl bromide in 1000 ml. of acetonitrile containing 32.0 g. (0.3M) of sodium carbonate and 100 ml. of water was stirred for one hour at 25° C. The precipitate that formed was collected by filtration, washed with water and with diethyl ether, and air dried to provide 8.0 g. of 1-(4-benzyloxyphenyl)-1-oxo-2-[1,1-dimethyl-3-(4-aminocarbonylphenyl)propylamino]ethane. M.P. 184°–187° C. This product was converted to the hydrochloride. salt by reaction with hydrogen chloride in diethyl ether. M.P. 219°–224° C.

The compound thus prepared was reacted with sodium borohydride in methanol to provide, following conversion to the hydrochloride salt and crystallization from methanol and diethyl ether, 5.8 g. of 1-(4-benzyloxyphenyl)-2-[1,1-dimethyl-3-(4-aminocarbonyl-phenyl)propylamino]ethanol hydrochloride. M.P. 141°–143° C.

Reaction of the above compound with hydrogen in the presence of Raney Nickel effected cleavage of the hydroxy protecting group to afford, following crystallization of the hydrochloride salt, 1.3 g. of 1-(4-aminocarbonylphenyl) propylamino]ethanol hydrochloride. M.P. 185° C. (dec.)

Analysis calc. for $C_{20}H_{27}ClN_2O_3$
Theory: C, 63.40; H, 7.18; N, 7.39; Cl, 9.36.
Found: C, 63.26; H, 7.0! ; N, 7.45; Cl, 9.42.

The compounds of Examples 13 and 14 were prepared by the general procedure of Example 12.

EXAMPLE 13

1-(2-Fluorophenyl)-2-[1,1-dimethyl-3-(4-aminocarbonylphenyl)propylamino]ethanol hydrochloride
M.P. 227°–230° C.

EXAMPLE 14

1-(3-Hydroxyphenyl)-2-[1,1-dimethyl-3-(4-hydroxyphenyl)propylamino]ethanol hydrobromide
M.P. 161°–165° C.

EXAMPLE 15

1-Phenyl-2-[1-methyl-3-(4-methylsulfonyl-phenyl) propylamino]ethanol hydrochloride Methyl 2-(4-methylthiophenyl)ethyl ketone was oxidized by reaction with m-chloroperbenzoic acid to give methyl 2-(4-methylsulfonylphenyl)ethyl ketone. A solution of 6.73 g. of 2-amino-1-phenylethanol and 11.10 g. of methyl 2-(4-methylsulfonylphenyl)ethyl ketone in 500 ml. of toluene containing 200 mg. of p-toluenesulfonic acid was heated at reflux for twenty-four hours. The reaction mixture was cooled and the solvent was removed by evaporation to give the Schiff base 1-phenyl-2-[1-methyl-3-(4-methylsulfonylphenyl)propylimino]ethanol. The Schiff base thus prepared was reacted with 3.7 g. of sodium borohydride in 500 ml. of ethanol at 0° C. for sixteen hours. The reaction mixture was diluted by addition of 50 ml. of acetone and 20 ml. of 3N hydrochloric acid. The mixture was concentrated to an oil by evaporation of the solvent. The oil crystallized upon standing at room temperature. Recrystallization of the product from 200 ml. of hot ethanol afforded 8.96 g. (48% yield) of 1-phenyl-2-[1-methyl-3-(4-methylsulfonylphenyl)propylamino]ethanol hydrochloride. M.P. 164°–170° C.

Analysis calc. for $C_{19}H_{26}ClNO_3S$

Theory: C, 59.44; H, 6.83; N, 3.65; Cl, 9.23; S, 8.35.

Found: C, 59.28; H, 6.57; N, 3.70; Cl, 9.36; S, 8.11.

EXAMPLE 16

Premix for Chickens

| Premix for Chickens | |
|---|---|
| Ingredient | % by weight |
| 1-(4-hydroxyphenyl)-2-[1,1-dimethyl-3-phenylpropylamino]-ethanol succinate | 25 |
| Ground Corn | 74 |
| Sodium Chloride | 1 |
| | 100 |

EXAMPLE 17

Premix for Ruminants

| Premix for ruminants | |
|---|---|
| Ingredient | % by weight |
| 1-(2-fluorophenyl)-2-[1,1-dimethyl-3-(4-aminocarbonyl-phenyl)propylamino]ethanol | 30 |
| Ground yellow corn | 60 |
| Alfalfa meal | 10 |
| | 100 |

EXAMPLE 18

Premix for Swine

| Premix for Swine | |
|---|---|
| Ingredient | % by weight |
| 1-(4-hydroxyphenyl)-2-[1-methyl-3-(4-hydroxyphenyl)propylamino]-ethanol hydrochloride | 10 |
| Soybean mill run | 88 |
| Mineral oil | 2 |
| | 100 |

The above ingredients are blended to uniformity to provide a dry flowable premix that can be admixed with a typical animal feed ration at a rate to provide about 20 ppm of active ingredient in the final feed ration. For example, the premix can be added to the following swine grower ration for convenient oral administration of the β-phenethanolamine to swine.

| Ingredient | % by weight | lbs/Ton |
|---|---|---|
| Corn, yellow, ground | 76.70 | 1534 |
| Soybean Oil Meal, solvent extracted, dehulled | 19.35 | 387 |
| Calcium Carbonate | 1.20 | 24 |
| Dicalcium Phosphate, feed grade | 1.20 | 24 |
| Salt (sodium chloride) | 0.50 | 10 |
| Trace mineral premix, AN-03[1] | 0.10 | 2 |
| Swine Vitamin Premix, SW-03[2] | 0.65 | 13 |
| Vitamin A Premix, 3M USP units/lb.[3] | 0.05 | 1 |
| Methionine Hydroxy Analogue, 93% | 0.20 | 4 |
| Selenium Premix[4] | 0.005 | 1 |
| | 100.00 | 2000 |

[1]Each Kg of premix contains: 50 g. manganese as manganses sulfate; 100 g. zinc as zinc carbonate; 50 g. iron as ferrous fulfate; 5 g. copper as copper oxide; 1.5 g. iodine as potassium iodide and 150 g. maximum and 130 g. minimum calcium as calcium carbonate.
[2]Each Kg of premix contains: 77,161 IU Vitamin $D_2$; 2,205 IU Vitamin E; 411 gm. riboflavin; 1,620 mg. pantothenic acid; 2,205 mg. niacin; 4.4 mg. Vitamin $B_{12}$; 441 mg. Vitamin K; 19,180 mg. choline; 110 mg. folic acid; 165 mg. pyridoxine; 110 mg. thiamine; 22 mg. biotin.
[3]Each Kg of premix contains 6,613,800 IU Vitamin A.
[4]Each Kg of premix contains 200 mg. of selenium as sodium selenite.

EXAMPLE 19

| Feed Ration for Lambs | | |
|---|---|---|
| Ingredient | Percent | lbs/T |
| Yellow corn | 61.00 | 1220.0 |
| Corn cobs | 20.00 | 400.0 |
| Alfalfa Meal, dehydrated | 5.40 | 108.0 |
| Soybean oil meal | 8.00 | 160.0 |
| Urea, feed grade | 0.50 | 10.0 |
| Molasses, cane | 3.00 | 60.0 |
| Dicalcium phosphate | 0.43 | 8.6 |
| Salt | 0.30 | 6.0 |
| Calcium carbonate | 0.14 | 2.3 |
| Trace mineral premix[1] | 0.03 | 0.6 |
| Vitamin A + $D_3$ Premix[2] | 0.10 | 2.0 |
| Vitamin E Premix[3] | 0.10 | 2.0 |
| 1-(4-Hydroxyphenyl)-2-(1,1-dimethyl-3-phenylpropylamino)-ethanol | 1.00 | 20.0 |
| | 100.00 | 2000.0 |

[1]Trace mineral premix contains: 2.5% manganese as manganese oxide, 0.07% iodine as potassium iodide, 0.3% cobalt as cobalt carbonate, 0.5% copper as copper oxide, and 20.0% zinc as zinc sulfate.
[2]Each poind of vitamin A and $D_3$ premix contains 2,000,000 USP units Vitamin A and 225,750 USP units Vitamin $D_3$.
[3]Each pound of Vitamin E premix contains 20,000 IU Vitamin E.

The compounds to be employed in the method of this invention have demonstrated efficacy in animal tests designed to establish beneficial nutritional effects. In one test designed to show lipolytic activity, normal swine, either barrows or gilts, were employed to analyze the effect of compounds on blood glucose, insulin, and non-esterified fatty acids (NEFA).

Test animals were maintained in metabolism crates, and following a period of adaptation, catheters were placed in their femoral veins. Prior to administration of the test ccmpounds, all animals were fasted for a period of forty hours. Such fasting causes an elevation of NEFA's in the blood. On the day of the test, all animals were fed a normal feed ration, and one group of animals were held as controls while another group of animals received a test compound. The test compounds were administered at 200 mcg/kg intravenously, or orally at 1 mg/kg. Blood samples were taken from each animal immediately prior to treatment and then at one hour intervals for a period of six hours following treatment. The blood plasma was analyzed for glucose, insulin and NEFA content.

When the fasted pigs were fed the normal feed ration without a test compound, the NEFA levels in the blood drop dramatically and remained low. A β-phenethanolamine as defined herein caused either an elevation in NEFA's, or inhibited the drop in NEFA's. Blood levels of glucose and insulin were also elevated with the β-phenethanolamines.

The following Table presents the lipolytic activity of several preferred β-phenethanolamines when evaluated according to the test described above. The results are averages of several tests.

TABLE I

Lipolytic Activity (increase in NEFA's)

$$\text{R}^1\text{R}^2\text{-C}_6\text{H}_3\text{-CH(OH)CH}_2\text{NHC(R}^3\text{)(R}^4\text{)-CH}_2\text{CH}_2\text{-C}_6\text{H}_4\text{-R}^5$$

| $R^1$ | $R^2$ | $R^3$ | $R^4$ | $R^5$ | % increase in NEFA's over control | % increase in glucose over control |
|---|---|---|---|---|---|---|
| H | H | H | CH$_3$ | SO$_2$CH$_3$ | 131 | 9 |
| p-OH | H | CH$_3$ | CH$_3$ | H | 445 | 48 |
| m-OH | H | CH$_3$ | CH$_3$ | H | 71 | 31 |
| m-OH | H | CH$_3$ | CH$_3$ | F | 28 | 72 |
| p-OH | H | CH$_3$ | CH$_3$ | OH | 141 | 35 |
| p-OH | H | CH$_3$ | CH$_3$ | CONH$_2$ | 18 | 169 |
| m-OH | H | CH$_3$ | CH$_3$ | OH | 68 | 40 |
| H | H | H | H | NO$_2$ | 199 | 7 |
| p-OCH$_3$ | H | CH$_3$ | CH$_3$ | H | 84 | 25 |
| p-OCH$_3$ | H | CH$_3$ | CH$_3$ | OH | 249 | 5 |
| H | H | H | CH$_3$ | NO$_2$ | 1458 | 27 |

A ten day in vivo study was employed to determine the effect of β-phenethanolamines on feed efficiency and rate of growth. In these studies, barrows and gilts weighing approximately 60 kg were maintained in individual pens. Each treatment was replicated six times in randomly assigned animals, with each test animal forming an experimental unit. A group of control animals received a normal swine grower feed ration comprising the following ingredients:

| Ingredient | % by weight |
|---|---|
| Ground yellow corn | 76.70 |
| Soybean oil meal | 19.35 |
| Calcium carbonate | 1.20 |
| Dicalcium phosphate | 1.20 |
| Salt | 0.50 |
| Trace mineral premix | 0.10 |
| Swine Vitamin premix | 0.65 |
| Vitamin A premix, 3M USP units/lb. | 0.05 |
| Methionine Hydroxy analogue, 93% | 0.20 |
| Selenium premix | 0.05 |
| | 100.00 |

The test animals received the same feed ration plus the test compound. All animals received feed and water ad libitum. All animals were weighed on day 1 and again on day 10, and feed consumption was measured by recording all feed issued and any remaining feed on day 10. The results of two series of this 10 day test for several β-phenethanolamines are given in Table II. In the Table, the column labelled "ADG" is the average daily weight gain in pounds; "ADF" is the average daily feed consumption (in pounds) by the test animals; and F/G is the feed efficiency calculated as ADF divided by ADG.

TABLE II

Growth Promotion and Feed Efficiency $$\text{R}^1\text{R}^2\text{-C}_6\text{H}_3\text{-CH(OH)CH}_2\text{NHC(R}^3\text{)(CH}_3\text{)-CH}_2\text{CH}_2\text{-C}_6\text{H}_4\text{-R}^5$$

| | | $R^1$ | $R^2$ | $R^3$ | $R^5$ | dose ppm | ADG | ADF | F/G |
|---|---|---|---|---|---|---|---|---|---|
| Experiment I | Control | | | | | | 1.60 | 4.7 | 2.98 |
| | p-OH | H | H | OH | | 20 | 2.19 | 5.0 | 2.33 |
| | H | H | H | NO$_2$ | | 20 | 1.78 | 4.22 | 2.37 |
| Experiment II | Control | | | | | | 1.34 | 4.16 | 3.22 |
| | p-OH | H | CH$_3$ | H | | 20 | 1.60 | 4.26 | 2.66 |
| | m-OH | H | CH$_3$ | F | | 20 | 1.52 | 4.57 | 3.01 |

The β-phenethanolamines to be employed in the method of this invention can be administered in combination with other compounds known to have a beneficial effect upon animals. Typical compounds to be co-administered with the β-phenethanolamines include antibiotics, for example any of the tetracyclines, tylosin, penicillins, cephalosporins, polyether antibiotics, gycopeptides, orthosomycins and related compounds commonly administered to swine, poultry, ruminants and the like. A preferred combination to be employed in the present method is an antibiotic such as tylosin or a tetracycline, together with 1-(4-hydroxy-phenyl)-2-[1-methyl-3-(4-hydroxyphenyl)propylamino]-ethanol. Such combinations will comprise the respective components in a ratio of about 1 to about 2 parts by weight of β-phenethanolamine and about 1 to about 10 parts by weight of the partner component.

In a typical treatment, 1-(4-hydroxyphenyl)-2-[1-methyl-3-(4-hydroxyphenyl)propylamino]ethanol was evaluated in a 42-day study employing finishing swine. Each treatment was replicated four times, with three pigs per replication. All treatments included a normal feed diet plus tylosin at 40 g/T. The animals were tested for growth performance and feed efficiency enhancement. Carcass quality was determined by analysis for fat and muscling. The results of the study are given in Table III. Both β-phenethanolamine treatments resulted in improved growth performance and carcasses with less fat and more muscle.

TABLE IV

|  | Control | Tylosin | A | Tylosin + A |
|---|---|---|---|---|
| ADG | 1.63 | 1.64 | 1.36 | 1.50 |
| ADF | 5.64 | 5.77 | 5.10 | 5.38 |
| F/G | 3.46 | 3.51 | 3.77 | 3.59 |
| Slaughter Wt, (lbs) | 210 | 211 | 193 | 201 |
| Carcass Wt, (lbs) | 150.3 | 151.5 | 140.1 | 146.3 |
| Fat Depth, 10th rib, (in)[1] | 0.96 | 0.96 | 0.80 | 0.85 |
| Loin Eye Area (in$^2$)[1] | 4.60 | 4.68 | 4.92 | 5.00 |
| Est. % Muscle[2] | 49.2 | 49.2 | 51.4 | 51.2 |
| Est. Pounds Muscle[2] | 75.3 | 76.5 | 74.1 | 76.8 |

[1] These results are based upon measurement of fat at the 10th rib after the carcass is split in half across the backbone.
[2] A regression equation is employed in arriving at the numerical predictions of carcass muscle (J. Animal Science, 1977, Vol. 44:8–17).

As in the previous study, both phenethanolamine treatments resulted in carcasses with less fat and more muscle. It should also be noted that the estimated amount of carcass muscle produced with the Tylosin +A treatment was similar to that produced in the control and the Tylosin treatment alone. This result was achieved, however, with less feed consumption than either the control or the Tylosin treatments.

Additional studies have been carried out to demonstrate the anabolic effect of β-phenethanolamines in swine. The

TABLE III

Growth Promotion, Feed Efficiency and Carcass Quality

|  | Control[1] | β-phenethanolamine[2] | | | |
|---|---|---|---|---|---|
|  |  | 20 g/T | % change | 40 g/T | % change |
| ADG | 1.94 | 2.07 | (6.7) | 2.05 | (5.7) |
| ADF | 6.28 | 6.63 | (5.6) | 6.64 | (5.7) |
| F/G | 3.24 | 3.20 | (−1.2) | 3.24 | (0) |
| Live Wt. at Slaughter, lb | 217.0 | 223.0 | (2.8) | 221.0 | (1.8) |
| Chilled Carcass Wt., lb | 154.6 | 160.5 | (3.8) | 159.8 | (3.4) |
| Fat Depth at 10th Rib, in | 1.15 | 1.09 | (−5.2) | 1.05 | (−8.7) |
| Loin Eye Area Sp., in | 4.64 | 4.91 | (5.8) | 4.84 | (4.3) |
| Estimated pounds of Fat Free Muscles[3] | 74.2 | 78.8 | (6.1) | 78.4 | (5.7) |

[1] all diets contained 40 g/T of tylosin
[2] 1-(4-hydroxyphenyl)-2-[1-methyl-3-(4-hydroxyphenyl)propylamino]-ethanol hydrochloride
[3] A regression equation was employed in arriving at the numerical predictions of carcass muscle (J. Animal Science, 1977, Vol. 44:8–17).

The data reported in Table III further demonstrates that the β-phenethanolamines described herein promote growth, improve feed efficiency and improve leaness.

In a similar study conducted over a 61 day period, a group of control animals received a normal daily feed ration with no additive. Another group of animals received the feed ration plus tylosin at 40 g/T, while another group received the feed ration plus 1-(4-hydroxyphenyl)-2-[1-methyl-3-(4-hydroxyphenyl)-propylamino]ethanol hydrochloride (compound A) at 20 g/T. A final group of finishing swine received the feed ration plus the combination of 40 g/T of tylosin and 20 g/T of the pb. enethanolamine. The results of this trial are given in Table IV.

effect of the compounds on nitrogen retention in finishing barrows was determined. Nitrogen retention is the difference between nitrogen intake and nitrogen excreted. Increased nitrogen retention is known to be associated with increased anabolic activity, resulting in improved carcass muscling and leanness.

In a typical study, barrows weighing about 172 pounds (78 Kg) were orally administered various doses of 1-(4-hydroxyphenyl)-2-[1-methyl-3-(4-hydroxy-phenyl) propylamino]ethanol hydrochloride (Compound A). All animals received water and a constant amount of normal swine feed ration. The results of this study are presented in Table V, and show that all β-phenethanolamine treatments improved nitrogen retention compared to controls.

TABLE V

Nitrogen Retention

| Treatment | Animals per treatment | Nitrogen Retained (g/day) |
|---|---|---|
| Control | 6 | 21.0 |
| Compound A (5 g/T) | 3 | 23.6 |
| Compound A (10 g/T) | 3 | 23.9 |
| Compound A (20 g/T) | 3 | 25.0 |

As pointed out above, the method of this invention can be practiced with individual isomers of β-phenethanolamines or with mixtures of isomers and diastereomers. In a study to determine the effect on weight gain and feed efficacy of various mixtures of diastereomers, barrows initially weighing about 177 pounds were fed a normal swine diet plus a β-phenethanolamine at 20 g/T of feedstuff. Each treatment was replicated in twelve individually fed animals. The results are presented in Table VI and show that growth performance was improved by both β-phenethanolamine treatments with very little change in feed intake.

TABLE VI

| Treatment | Average Daily Feed (lbs) | Average Daily Gain (lbs) |
|---|---|---|
| Control | 5.89 | 1.58 |
| 1-(4-hydroxyphenyl)-2-[1-methyl-3-(4-hydroxyphenyl)propylamino]ethanol hydrochloride 57.5% RR,SS 42.5% RS,SR | 5.94 | 2.15 |
| 1-(4-hydroxyphenyl)-2-[1-methyl-3-(4-hydroxyphenyl)propylamino]ethanol hydrochloride 47% RR,SS 53% RS,SR | 5.86 | 1.95 |

The data in Table VI demonstrates that the method of improving feed efficency and promoting growth can be practiced with any desired mixture of β-phenethanolamine optical isomers.

The efficacy of the β-phenethanolamines described herein also has been demonstrated in poultry. In a typical study, broilers that were twenty-one days old were administered an oral dosing of a β-phenethanolamine in their normal daily feed ration. All animals received the following broiler finisher ration:

| Ingredients | % by weight | lbs/T |
|---|---|---|
| Ground yellow corn | 66.40 | 1328.00 |
| Animal vegetable fat | 1.53 | 30.60 |
| Corn Glut. meal (60%) | 4.00 | 80.00 |
| Soybean meal (48%) | 19.19 | 383.80 |
| Fish meal-menhaden | 2.50 | 50.00 |
| Dicalcium phosphate | 1.01 | 34.20 |
| Feather meal-Hydr. | 2.50 | 50.00 |
| Ground limestone | 0.83 | 16.60 |
| Salt | 0.30 | 6.00 |
| Vitamin Premix[1] | 0.50 | 10.00 |
| Trace mineral premix[2] | 0.10 | 2.00 |
| Methionine Hyd. Anal. | 0.15 | 3.00 |
| Lysine HCl | 0.29 | 5.80 |
| | 100.00 | 2000.00 |

[1]Vitamin premix provides 3000 IU of vitamin A, 900 ICU of vitamin $D_3$, 40 mg. of vitamin E, 0.7 mg. of vitamin K, 1000 mg of choline, 70 mg. of niacin, 4 mg of pantothenic acid, 4 mg of riboflavin, 100 mcg of vitamin $B_{12}$, 100 mcg of biotin and 125 mg of ethoxyquin per kg of complete feed.

[2]Trace mineral premix provides 75 mg of manganese, 50 mg of zinc, 25 mg of iron and 1 mg of iodine per kg of complete feed.

Test animals received with the above ration varying doses of 1-(4-hydroxyphenyl)-2-[1-methyl-3-(4-hydroxyphenyl) propylamino]ethanol hydrochloride (compound A). Each treatment was replicated sixteen times, and the test was terminated when the animals reached fifty-six days of age. The animals were analyzed for weight gain and feed efficiency. The results of this test in broilers is presented in Table VII as mean weight gain and mean feed to gain ratios.

TABLE VII

Growth Performance of Broilers

| Treatment | Dose (g/T) | Weight Gain grams | Weight Gain % improvement | Feed Efficiency Feed/Gain Ratio | Feed Efficiency % change from control |
|---|---|---|---|---|---|
| Control | | 1473 | 0 | 2.336 | 0 |
| Compound A | 10 | 1585 | 7.6 | 2.292 | 1.9 |
| Compound A | 20 | 1613 | 9.5 | 2.298 | 1.6 |
| Compound A | 40 | 1550 | 5.2 | 2.312 | 1.0 |
| Compound A | 80 | 1669 | 13.3 | 2.221 | 4.9 |

The results of this study demonstrate that the β-phenethanolamines described herein are effective in promoting growth and improving feed efficiency in poultry.

The compounds of the invention also have demonstrated efficacy in ruminants. Forty-eight cross-bred wether lambs were employed in a test designed to show the effects of Compound A (1-(4-hydroxyphenyl)-2-[1-methyl-3-(4-hydroxyphenyl)propylamino]ethanol hydrochloride) at varying doses. Sixteen animals were held as controls, while sixteen received 40 ppm of Compound A, and another sixteen received 80 ppm of Compound A. All animals received a normal daily feed ration and water ad libitum.

Average daily weight gain and average daily feed consumption after twenty-eight days is given below in Table VIII. The data demonstrates that a β-phenethanolamine as defined herein is effective in promoting growth and improving feed efficiency in ruminants.

TABLE VIII

| Treatment | Growth Performance of Lambs | | | |
|---|---|---|---|---|
| | Dose (ppm) | ADG (lbs) | ADF (lbs) | F/G |
| Control | 0 | 0.414 | 3.68 | 8.89 |
| Compound A | 40 | 0.418 | 3.61 | 8.64 |
| Compound A | 80 | 0.472 | 3.57 | 7.56 |

We claim:

1. A composition useful for treating a domesticated warm blooded animal to promote growth, improve feed efficiency, or improve leanness, which comprises both of (1) a first compound having the formula

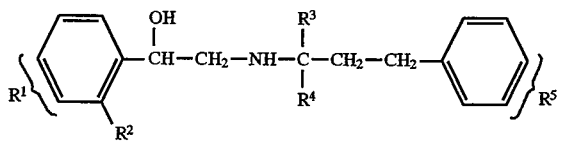

wherein:

$R^1$ is hydrogen, hydroxy, or methoxy;
$R^2$ is hydrogen or fluoro;
$R^3$ is hydrogen or $C_1$-$C_2$ alkyl;
$R^4$ is hydrogen or methyl;
$R^5$ is hydrogen, fluoro, nitro, hydroxy, $SO_2CH_3$ or $CONH_2$; provided that $R^1$ is hydrogen only when $R^5$ is nitro or $SO_2CH_3$, or an acid addition salt thereof; and (2) a second compound which is a tetracycline, tylosin, penicillin, cephalosporin, polyether, glycopeptide, or orthosomycin, in a ratio of about 1 to about 2 parts by weight of the first compound and about 1 to about 10 parts by weight of the second compound.

2. The composition of claim 1 wherein the first compound is 1-(4-hydroxyphenyl)-2-(1-methyl-3-(4-hydroxyphenyl)propylamino)ethanol or an acid addition salt thereof.

3. The composition of claim 2 where the second compound is tylosin.

4. The composition of claim 2 wherein the second compound is a polyether.

5. A method for treating a domesticated warm blooded animal to promote growth, improve feed efficiency, or improve leanness, which comprises administering to the animal both of (1) a first compound having the formula

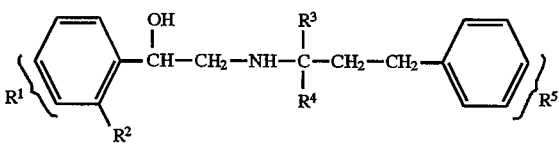

wherein:

$R^1$ is hydrogen, hydroxy, or methoxy;
$R^2$ is hydrogen or fluoro;
$R^3$ is hydrogen or $C_1$-$C_2$ alkyl;
$R^4$ is hydrogen or methyl;
$R^5$ is hydrogen, fluoro, nitro, hydroxy, $SO_2CH_3$ or $CONH_2$; provided that $R^1$ is hydrogen only when $R^5$ is nitro or $SO_2CH_3$, or an acid addition salt thereof; and (2) a second compound which is a tetracycline, tylosin, penicillin, cephalosporin, polyether, glycopeptide, or orthosomycin, in amounts which in combination are effective.

6. The method of claim 5 wherein the first compound is 1-(4-hydroxyphenyl)-2-(1-methyl-3-(4-hydroxyphenyl)-propylamino)ethanol or an acid addition salt thereof.

7. The method of claim 6 wherein the second compound is tylosin.

8. The method of claim 6 wherein the second compound is a polyether.

* * * * *